(12) United States Patent
Cattaneo (10) Patent No.: US 9,320,558 B2
(45) Date of Patent: Apr. 26, 2016

(54) SYSTEM AND METHOD FOR THE QUALITY CONTROL OF SCREWED-IN JOINTS

(75) Inventor: Massimiliano Cattaneo, Carate Brianza (IT)

(73) Assignee: ATLAS COPCO BLM S.R.L., Paderno Dugnano (MI) (IT)

( * ) Notice: Subject to any disclaimer, the term of this patent is extended or adjusted under 35 U.S.C. 154(b) by 492 days.

(21) Appl. No.: 13/813,484

(22) PCT Filed: Aug. 2, 2011

(86) PCT No.: PCT/IB2011/001800
§ 371 (c)(1),
(2), (4) Date: Mar. 25, 2013

(87) PCT Pub. No.: WO2012/017295
PCT Pub. Date: Feb. 9, 2012

(65) Prior Publication Data
US 2013/0211413 A1  Aug. 15, 2013

(30) Foreign Application Priority Data
Aug. 2, 2010  (IT) .............................. MI2010A1455

(51) Int. Cl.
*A61B 17/88* (2006.01)
*B25B 23/142* (2006.01)

(52) U.S. Cl.
CPC ......... *A61B 17/8875* (2013.01); *B25B 23/1425* (2013.01)

(58) Field of Classification Search
None
See application file for complete search history.

(56) References Cited

U.S. PATENT DOCUMENTS

2009/0078057 A1* 3/2009 Schultz ............... B25B 23/1425
73/862.23

FOREIGN PATENT DOCUMENTS

WO  2009039497 A2  3/2009
WO  2010047638 A1  4/2010

OTHER PUBLICATIONS

International Search Report Dated Dec. 7, 2011.

* cited by examiner

*Primary Examiner* — Robert R Raevis
(74) *Attorney, Agent, or Firm* — Hedman & Costigan, P.C.; James V. Costigan; Kathleen A. Costigan (57) ABSTRACT

The present invention refers to a system for the quality control of screwed-in joints, where the system has:
a dynamometric wrench having a lever body provided, at one end, with a handle and, at the opposite end, with a coupling head having a sensor for detecting the torque applied to the threaded tightening element and a sensor for detecting the rotation angle of the lever body,
a first interface and
a processing unit
wherein the processing unit is capable of detecting, torque and a corresponding rotation angle of the lever body.

20 Claims, 5 Drawing Sheets

SYSTEM AND METHOD FOR THE QUALITY CONTROL OF SCREWED-IN JOINTS

The present invention refers to a system and method for the quality control of screwed-in joints through the use of a dynamometric wrench.

In particular, the present invention refers to a system using a dynamometric wrench that permits to determine, in real time, the residual torque or residual couple, i.e. the residual torque or the actual tightening couple of a screwed-in joint, in order to control the effectiveness of tightening of an automatic screwier and/or the correct tightening of a joint.

Object of the present invention is also a method for controlling the quality of screwed-in joints.

Electronic dynamometric wrenches are known, which permit to acquire the data relating to the torque curve (couple) in function of time, from the analysis of which the residual torque (residual couple) is extrapolated through different analysis methods known to the man skilled in the art. Among these, in particular, the so-called "breakaway" method, which is based on identifying the moment when the threaded tightening element (nut or bolt) begins to move uninfluenced by static friction.

The data acquired with the known dynamometric wrenches are, however, affected by the expertise and experience of the operator who performs the measurement and, in particular, depend on the speed and regularity with which he applies the torque to the threaded tightening element of the joint tested and on the moment when he ends the test.

A further drawback of the known dynamometric wrenches consists of the fact that they permit an analysis of the torque curve (couple)/time in times different from those of acquisition of the same.

All of this often translates into the application of an excessive tightening over-torque to the tested joint.

The purpose of the present invention is that to avoid the drawbacks of the prior art indicated above by providing a system and a method for the quality control of screwed-in joints that permit to obtain, in real time, the residual torque, i.e. the actual tightening torque or couple of a screwed-in joint, in order to control the effectiveness of tightening of an automatic screwier and/or the correct tightening of a joint, avoiding an excessive over-torque being applied to the tested joint.

Another purpose of the present invention is to provide a system and method for the quality control of screwed-in joints that permit to detect the residual torque or the residual couple of the tested joint with a high degree of reliability regardless of the expertise and experience of the single operator and the ways in which the test is carried out.

These and other further purposes are accomplished through a system as defined in claim 1.

Further characteristics are defined in the dependent claims 2-11.

These and other further purposes are also accomplished through a method for the quality control of screwed-in joints as defined in claim 13.

The characteristics and advantages of a system and method for the quality control of a screwed-in joint according to the present invention will become clearer from the following description, exemplifying and not limiting, referring to the attached schematic drawings, wherein.

With particular reference to the attached figures, a system for the quality control of screwed-in joints has been wholly indicated with 1.

The system 1 comprises a dynamometric wrench, the lever body 2 of which is provided, at one end, with a handle 3 for gripping and maneuvering by a user and, at the opposite end, with a coupling head 4 with the threaded tightening element of a joint to be controlled. The head 4 is provided, in a known way, with an attachment 5 to the nut or to the head of the screw that tightens a joint to be tested.

With the body 2 both sensor means 6 of the torque applied to the threaded element, and sensor means 7 of the rotation angle undergone by the lever body 2 in applying the torque to the threaded tightening element are also associated.

The sensor means 6 of the torque are suitable for supplying an output signal corresponding to the torque applied to the threaded tightening element by the lever body 2.

The sensor means 7 of the rotation angle of the lever body 2 are of the gyroscope type 8 and are suitable for supplying an output signal corresponding to the rotation angle of the lever body 2 in applying a torque to the threaded tightening element.

The sensor means 6 and 7 are not described any further in detail, being known to the man skilled in the art.

A processing unit 9 is in communication with the sensor means 6 of the torque and with the sensor means 7 of the rotation angle of the lever body 2, from which it receives in input the respective output signals.

Figure 1:
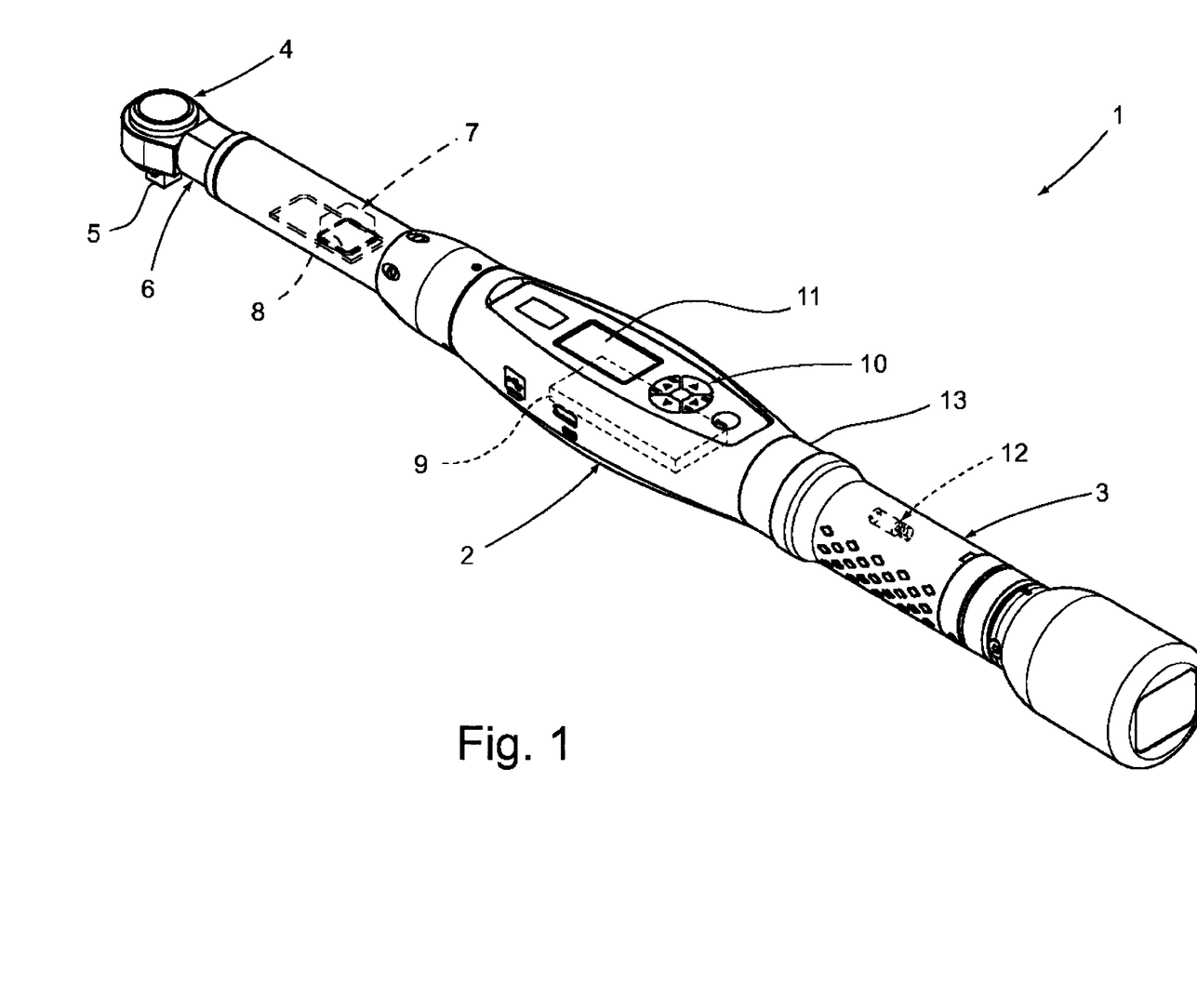
FIG. 1 is a schematic view of a system according to the present invention integrated in the body of a dynamometric wrench.
Figure 2:
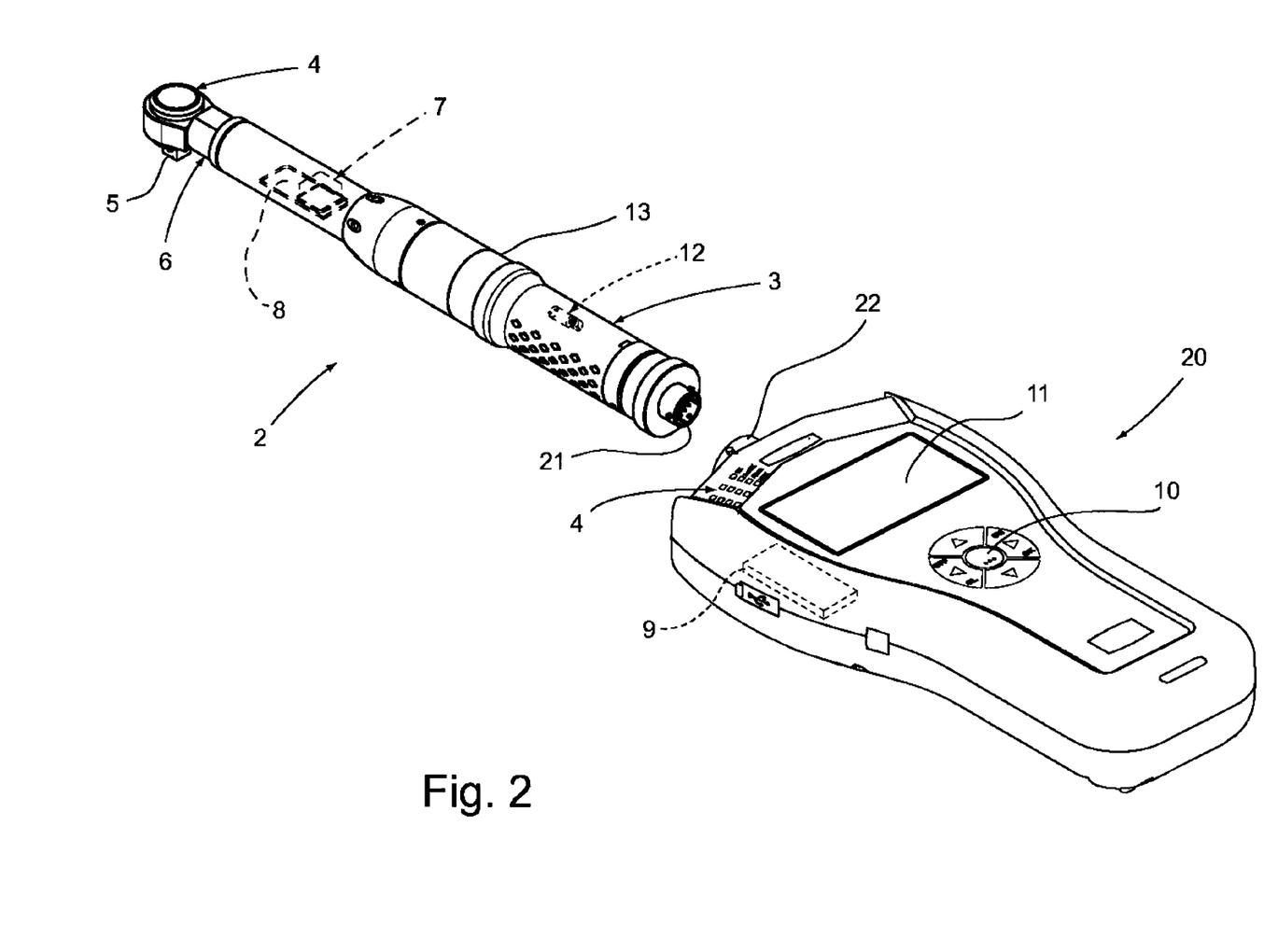
FIG. 2 is a schematic view of an alternative embodiment of a system according to the present invention.

In particular, the processing unit 9 can be integrated in the lever body 2 (FIG. 1) or can be integrated in a separate body 20 connectable to the lever body 2 through a cable, not shown, coupable to the connectors 21 and 22 respectively obtained at an end of the lever body 2 and of the separate body 20 (FIG. 2).

First and second interface means with a user are also present, which are in communication with the processing unit 9 and which, in the first embodiment, are both associated with the lever body 2 and which, in the second embodiment, are respectively associated with the lever body 2 and with the separate body 20.

In particular, the second interface means comprise a control and data entry keypad 10 and a display 11, whereas the first interface means comprise signalling means to a user of the type for example of vibration means 12, optical indicators 13, of the LED type for example, and means for emitting acoustic signals, not represented in detail. Advantageously, optical indicators can also be integrated in the body 20.

For the sake of simplicity of representation, in FIGS. 1 and 2 the connections and linkages between the processing unit 9, the sensor means 6 and 7 and the interface means are not represented.

According to the peculiar characteristic of the present invention, the processing unit 9 is suitable for detecting, among the pairs of values consisting of torque and corresponding rotation angle of the lever body 2 acquired by the respective sensor means 6 and 7, the pair of values corresponding to the moment when the threaded tightening element begins to move and discriminating, among the pairs of values subsequent to and comprising the pair of values of the start of the movement so detected and comprised in a predefinable variability range of the rotation angle of the lever body 2, the pair of values consisting of the residual torque and the corresponding rotation angle of the lever body 2.

More specifically, the processing unit 9 is capable of operating in real time with the use of the wrench for controlling a screwed-in joint and of commanding the signalling means to signal to a user the detection of the pair of values consisting of the residual torque and the corresponding rotation angle of the lever body 2.

In order to detect the pair of values corresponding to the moment when the threaded tightening element begins to move, the processing unit 9 carries out the following steps consisting of:

processing the pairs of values consisting of torque and corresponding rotation angle $(T_i, A_i)$ of the lever body 2 acquired by the respective sensor means 6 and 7 in order to obtain pairs of values consisting of the average values of torque and corresponding rotation angle of the lever body 2 $(T_m, A_m)$;

processing the pairs consisting of the average values $(T_m, A_m)$ of torque and corresponding rotation angle of the lever body 2 so obtained in order to determine the angular coefficient $(\alpha_t)$ of the curve given by the average values of torque $(T_m)$ in function of the corresponding average values of rotation angle $(A_m)$ of the lever body 2, processing the values of angular coefficient $(\alpha_t)$ so obtained in order to obtain an average value of the angular coefficient $(\alpha_m)$.

In a preferred embodiment, the processing of the pairs of values consisting of torque and corresponding rotation angle $(T_i, A_i)$ of the lever body 2 acquired by the respective sensor means 6 and 7 in order to obtain the pairs of average values $(T_m, A_m)$, comprises applying to the pairs of values $(T_i, A_i)$ a moving "window" average having width equal to I samples in order to obtain pairs of values consisting of the average values of torque and corresponding rotation angle of the lever body $(T_m, A_m)$, where $$T_m = \frac{\sum_{i=1}^{I} T_i}{I} \text{ and } A_m = \frac{\sum_{i=1}^{I} A_i}{I}$$

and I is preferably equal to 20.

The pairs of average values of torque and corresponding rotation angle of the lever body 2 $(T_m, A_m)$ so determined are processed through the application of a linear regression according to the formula:

$$\alpha_t = \left(\left(\sum_{m=1}^{M} T_m \times A_m\right) - \frac{\sum_{m=1}^{M} T_m \times \sum_{m=1}^{M} A_m}{M}\right) / \left(\left(\sum_{m=1}^{M} A_m^2\right) - \frac{\sum_{m=1}^{M} A_m \times \sum_{m=1}^{M} A_m}{M}\right)$$

Where M is preferably equal to 6.

From the $\alpha_t$ values so obtained an average $\alpha_m$ value is extrapolated by applying a moving "window" average having width equal to T samples according to the formula:

$$A_m = \frac{\sum_{t=1}^{T} A_t}{T}$$

Where T is preferably equal to 6.

Figure 4:
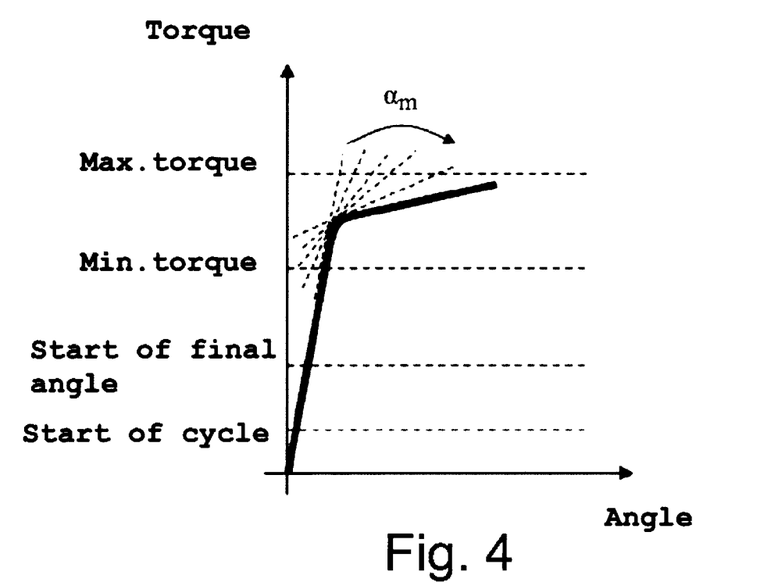
FIG. 4 schematically shows a first possible shape of the torque curve applied to a screwed-in joint by a dynamometric wrench in function of the rotation angle of the wrench itself, wherein a first method according to the present invention is schematised, for determining the pair of values corresponding to the moment when the threaded tightening element begins to move, i.e. the point at which the curve changes gradient.
Figure 5:
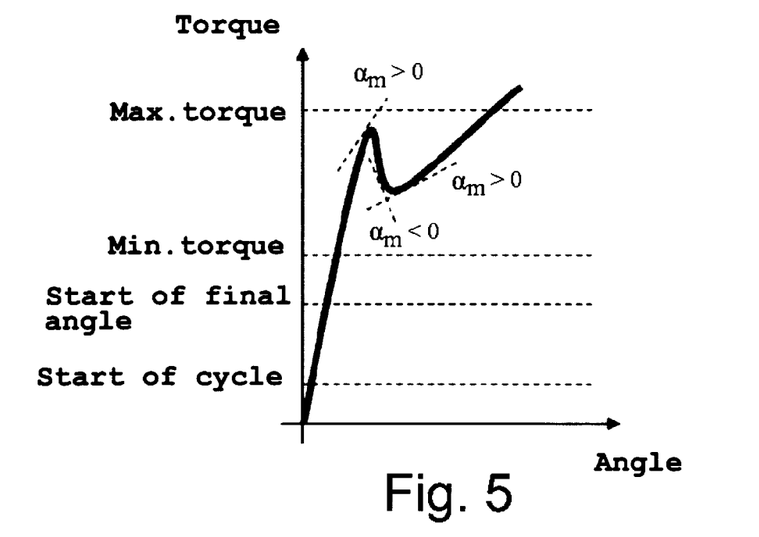
FIG. 5 schematically shows a second possible shape of the torque curve applied to a screwed-in joint by a dynamometric wrench in function of the rotation angle of the wrench itself.

The average values $(\alpha_m)$ of the angular coefficient of the curve given by the values of torque applied to the threaded tightening element by the lever body 2 and by the rotation angle undergone by the lever body 2 and/or the pairs of average values of torque and corresponding rotation angle of the lever body 2 $(T_m, A_m)$ are processed to identify the pair of values consisting of the residual torque and the corresponding rotation angle corresponding to the so-called breakaway point. As known, the curve that shows the values of torque applied to the threaded tightening element by the lever body 2 in function of the rotation angle undergone by the lever body 2 has two typical shapes schematically represented in FIGS. 4 and 5.

In the first case (FIG. 4), at the breakaway point the curve undergoes a variation in gradient, such a case is the most frequent.

In the second case (FIG. 5), the curve also presents inflections, this is the typical case of a stiff joint not well lubricated.

The system 1 according to the present invention discriminates the two cases and identifies for each of them the pair of values of residual torque and of the corresponding rotation angle of the lever body 2 (breakaway point).

In particular, in a first possible embodiment, the processing unit 9, in order to determine the moment when the threaded tightening element begins to move, i.e. the point at which the curve changes gradient, processes the average values of angular coefficient $(\alpha_m)$ by carrying out the steps consisting of:

discriminating among the obtained average values of angular coefficient $(\alpha_m)$ a sequence of N strictly decreasing values, where N is preferably equal to 7; i.e. the average values of angular coefficient $(\alpha_m)$ are examined in a moving "window" of N successive values until a sequence of N strictly decreasing values is identified $$\alpha_{m-N+1} > \alpha_{m-N+2} > \ldots > \alpha_{m-2} > \alpha_{m-1} > \alpha_m$$

verifying whether the percentage variation among the average values of angular coefficient $(\alpha_m)$ corresponding to the extremes of the sequence of N values so identified exceeds a predefinable threshold ($\delta$%); in particular it is verified if $$(\alpha_{m-N+1} - \alpha_m) > (\alpha_{m-N+1} * \delta) \backslash 100$$

where N is preferably equal to 7 and $\delta$ is equal to 50,
in the positive case, i.e. if the percentage variation between the average values of angular coefficient $(\alpha_m)$ corresponding to the extremes of the identified sequence of N strictly decreasing values exceeds the predetermined threshold, identifying an angular coefficient intermediate between such extreme values and attributing to the pair of values corresponding to the moment when the threaded tightening element begins to move, the values of average torque ($T_m$) and the corresponding average rotation angle ($A_m$) of the lever body 2 corresponding to the intermediate angular coefficient; in the case in which, for example, N=7, the intermediate angular coefficient is selected in the angular coefficient $\alpha_{m-3}$;

in the negative case, i.e. if the percentage variation between the average values of angular coefficient ($\alpha_m$) corresponding to the extremes of the identified sequence of N strictly decreasing values does not exceed the predetermined threshold, repeating the verification for a subsequent sequence of N strictly decreasing values.

Figure 6:
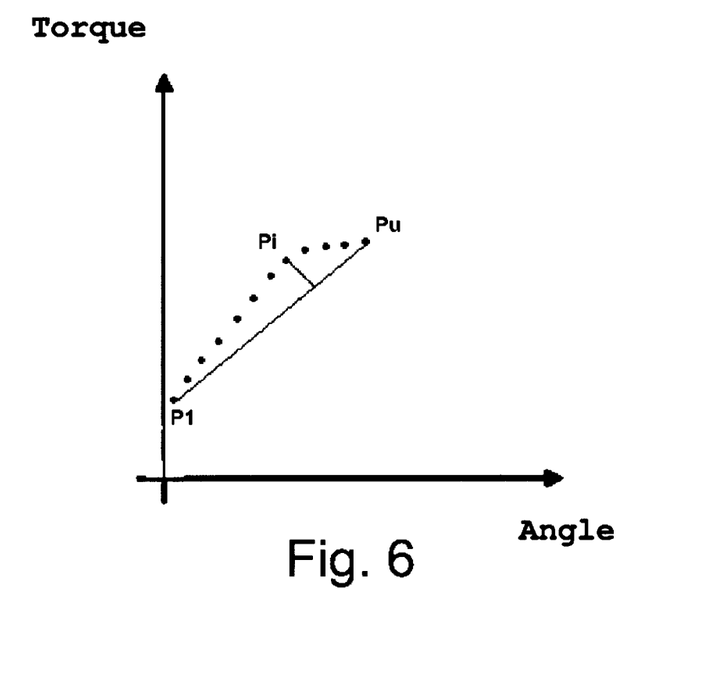
FIGS. 6 and 7 schematically show an alternative embodiment of the method according to the present invention to determine the pair of values corresponding to the moment when the threaded tightening element begins to move, i.e. the point at which the torque curve applied to a screwed-in joint by a dynamometric wrench in function of the rotation angle of the wrench itself changes gradient.
Figure 7:
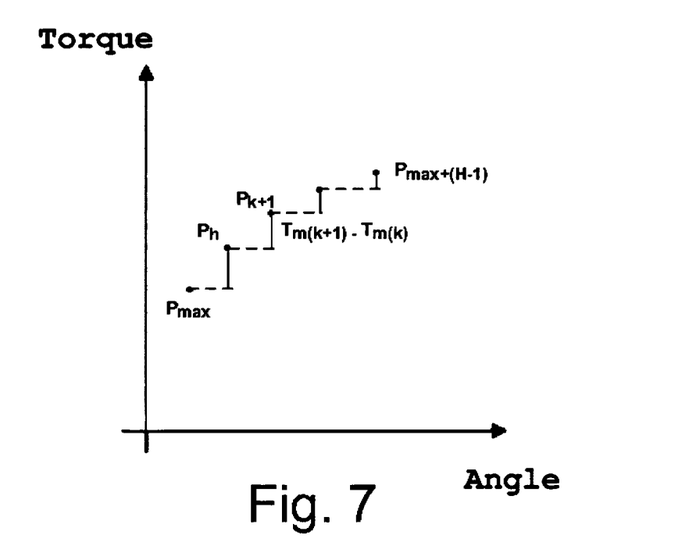

In a second possible embodiment (FIGS. 6 and 7), the processing unit 9, in order to determine the moment when the threaded tightening element begins to move, i.e. the point at which the curve changes gradient, processes the average values of angular coefficient ($\alpha_m$) carrying out the steps consisting of:

considering pairs of values $P_i=(Tm, Am)_i$ consisting of the average values of torque and corresponding rotation angle of the lever body ($T_m$, $A_m$) by successive increments $\Delta A$ of the rotation angle of the lever body, where $\Delta A$ is preferably equal to 0.1 degree;

for each pair $P_i=(Tm, Am)_i$ determining the distance Di of the point identified by it from the straight line that joins the first of the pairs $P_1=(Tm, Am)_1$ with the last of the pairs $P_u=(Tm, Am)_u$ according to the following formula:

$$Di=(A_{mu}-A_{m1})\times(T_{m1}-T_{mi})-(A_{m1}-A_{mi})\times(T_{mu}T_{m1})$$

selecting among the pairs $P_i=(Tm, Am)_i$ the one $P_{max}$ the value of said distance Di of which is the greatest ($D_{max}$);

discriminating in a window of H pairs of values $P_i=(Tm, Am)_i$ subsequent to and comprising $P_{max}$, where H is preferably equal to 5, i.e. from $P_{max}=(Tm, Am)_{max}$ to $P_{max+H}=(Tm, Am)_{max+H}$ the pair $P_D=(Tm, Am)_D$ the gradient of which is the lowest according to the following formula:

$$\min(T_{m(k+1)}-T_{m(k)}) \text{ with } \max<k<\max+(H-1)$$

for every acquired pair $P_i=(Tm, Am)_i$ repeating the previous steps and checking whether for the subsequent acquired X pairs $P_i=(Tm, Am)_i$, where X is preferably equal to 20, the current value of $P_D$ coincides with that determined for the previous pair $P_i=(Tm, Am)_i$ and, in the positive case, attributing to the pair of values corresponding to the moment when the threaded tightening element begins to move, the values of average torque ($T_m$) and the corresponding average rotation angle ($A_m$) of such pair $P_D=(Tm, Am)_D$.

Once, as indicated above, the pair of values of torque and of corresponding rotation angle of the lever body 2 corresponding to the moment when the threaded tightening element begins to move has been identified, it is taken, temporarily, as breakaway couple, i.e. as the pair of values consisting of the residual torque and the corresponding rotation angle of the lever body 2.

The processing unit 9 then carries out a step of verifying whether, in a number P of average values of angular coefficient ($\alpha_m$) subsequent to the first identified sequence of N strictly decreasing values or subsequent to the pair $P_D=(Tm, Am)_D$, the average values of the angular coefficient ($\alpha_m$) are all positive, i.e. if the curve showing the torque applied to the threaded tightening element in function of the rotation angle of the lever body 2 does not present inflections. Preferably, P is equal to 30.

In the positive case (FIG. 4), i.e. if all of the P average values of angular coefficient ($\alpha_m$) subsequent to the identified sequence of N strictly decreasing values are positive, then the pair identified as that corresponding to the moment when the threaded tightening element begins to move is confirmed as the pair of values consisting of the residual torque and the corresponding rotation angle of the lever body 2 (breakaway point).

In the negative case (FIG. 5), i.e. if some of the P average values of the angular coefficient ($\alpha_m$) subsequent to the identified sequence of N strictly decreasing values or subsequent to the pair $P_D=(Tm, Am)_D$ become negative and, therefore, the curve presents inflections, then starting from the negative average value of the angular coefficient ($\alpha_m$), the processing unit 9 carries out a step of controlling the average values of the angular coefficient ($\alpha_m$) in a moving "window" of R values, where R is preferably equal to 6, in order to discriminate a sequence of Q values wherein said average values of angular coefficient ($\alpha_m$) return to be positive and strictly increasing, where Q is preferably equal to 3.

Once such a sequence of Q positive and strictly increasing values of the average values of the angular coefficient ($\alpha_m$) has been identified, the first of them is identified as corresponding to the breakaway point, so that to the pair of values consisting of the residual torque and the corresponding rotation angle of the lever body 2 the values of torque and of the corresponding rotation angle of the lever body 2 corresponding to such a point are attributed. From the processing above indicated the decreasing angle values that represent only a noise are excluded.

As soon as the breakaway point, i.e. the pair of values consisting of the residual torque and the corresponding rotation angle of the lever body 2, has been identified, the processing unit 9 activates the signalling means, consisting in particular of the vibration means 12 and the optical indicators 13 (LED), to warn the user in order for him not to continue to rotate the wrench 1 avoiding an excessive tightening being applied on the threaded element. It is also possible that the user has interrupted the control test, i.e. has stopped rotating the wrench 1, prior to the detecting of the breakaway point.

After the user has stopped rotating the wrench 1, the processing unit 9 deactivates the signalling means earlier activated and verifies whether the value of the torque lastly detected falls within the range of values set as acceptable. In the negative case, it correspondingly activates dedicated signalling means, for example it activates a LED indexed as "High Led", if the value of the torque lastly detected exceeds the set maximum limit value, or a LED indexed as "Low Led", if the value of the torque lastly detected is lower than the set minimum limit value.

In the case in which the value of the torque lastly detected falls within the range of values set as acceptable, the processing unit activates the relative dedicated signalling means, consisting of for example an acoustic emitter.

In this last case, finally, the processing unit 9 activates the signalling means to indicate whether the value of the torque lastly detected corresponds to the value of residual torque or not; for example, if the value of the torque lastly detected is the residual torque, then a LED indexed as "OK Led" is activated, and in the opposite case the "Low Led" is activated.

Figure 3:
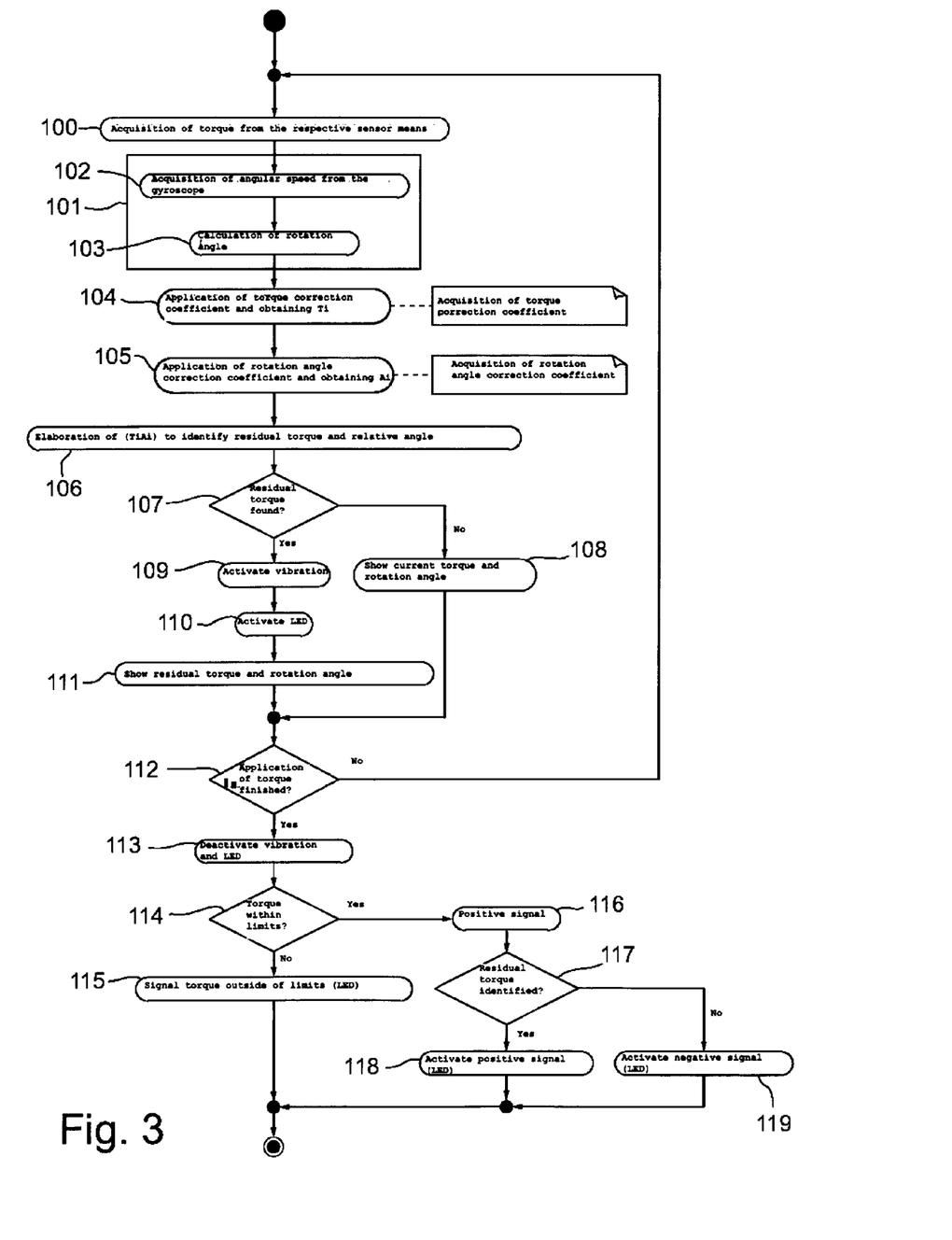
FIG. 3 is a flowchart of the operations carried out by the system in real time by using the dynamometric wrench for the quality control of a screwed-in joint.

With reference to FIG. 3, the operative steps of a method for the quality control of a screwed-in joint carried out using a system 1 according to the present invention are now explained.

A user applies a torque to the threaded element (nut or bolt) through the dynamometric wrench, tightening the joint to be controlled.

During such application, the processing unit 9 acquires, in real time, the values of torque $T_i$ (step 100) from the sensor means 6 and of the corresponding rotation angle $A_i$ of the lever body 2 from the sensor means 7 (step 101). This last step 101 in turn comprises the step 102 consisting of acquiring the value of the angular speed through the gyroscope 8 and the step 103 consisting of integrating the angular speed acquired in time.

In steps 104 and 105 the acquired values of $T_i$ and $A_i$ are corrected with suitable correction coefficients acquired from the application head 4 of the torque, from the sensor means of the torque and from the sensor means of the rotation angle of the lever body 2.

In step 106 the processing unit 9 processes the values of $T_i$ and $A_i$ according to the phases and the steps as described above in order to identify the breakaway point, i.e. the pair of values consisting of the residual torque and the corresponding rotation angle of the lever body 2. In step 107 it is controlled whether the pair of values consisting of the residual torque and the corresponding rotation angle of the lever body 2 (breakaway point) has been identified or not.

In the negative case, the processing unit 9 sends to the display 11 the current values of torque and of the corresponding rotation angle of the lever body 2 (step 108).

In the positive case, the processing unit 9 activates the signalling means and in particular the vibration means 12 (step 109) and the display means 13 (step 110) and sends to the display 11 the values of residual torque and of the corresponding rotation angle of the lever body 2 so identified (step 111).

Once it has been verified whether the user has stopped applying the torque to the threaded tightening element through the wrench 1 (step 112), the processing unit 9 deactivates (step 113) the signalling means (vibration means 12 and display means 13, 13') possibly activated and controls whether the last acquired value of torque falls or not within the set range of acceptable values (step 114).

In the negative case, the processing unit 9 activates the dedicated signalling means to signal whether such a value exceeds the maximum limit value or is lower than the minimum limit value (step 115). In the positive case, the processing unit 9 activates the dedicated signalling means to signal that such a value falls within the range of acceptable values (step 116) and, once it has been verified (step 117) whether such a value has been identified as residual torque (breakaway), it activates the dedicated signalling means to signal respectively whether such a value has been identified as residual torque (for example an "Ok Led") or the contrary case (for example with a "Low Led") (steps 118 and 119).

The system and method for the quality control of a screwed-in joint according to the present invention have the advantage of supplying, in real time, the value of the residual torque and of the relative rotation angle (breakaway point) independently of the expertise and experience of the operators, avoiding an excessive over-torque being applied.

The system thus conceived can undergo numerous modifications and variants, all of which covered by the invention; moreover, all details can be replaced by technically equivalent elements. Practically, the materials used, as well as the sizes, can be whatever according to the technical requirements.

The invention claimed is:

1. A system (1) for the quality control of screwed-in joints, comprising:
   a dynamometric wrench comprising a lever body (2) provided, at one end, with a handle (3) and, at the opposite end, with a coupling head (4) with the threaded tightening element of a joint to be controlled, sensor means (6) of the torque applied to said threaded tightening element which are associated with said lever body (2) and which are suitable for supplying an output signal corresponding to the torque applied to said threaded tightening element from said lever body (2) and sensor means (7) of the rotation angle of said lever body (2) which are associated with said lever body (2) and which are suitable for supplying an output signal corresponding to the rotation angle of said lever body (2) in applying said torque,
   first interface means (12, 13) with a user which are associated with said lever body (2) and
   a processing unit (9) which is in communication with said sensor means (6) of the torque and said sensor means (7) of the rotation angle of said lever body (2), from which it receives in input the respective output signals, and with said first interface means (12, 13), characterized in that said processing unit (9) is capable of detecting, between the pairs of values consisting of torque and corresponding rotation angle of the lever body (2) acquired by said respective sensor means (6, 7), the pair of values corresponding to the moment when said threaded tightening element begins to move and discriminating, among the pairs of values subsequent to and comprising the pair of values of the start of the movement so identified and comprised in a predefinable variability range of said rotation angle of said lever body, the pair of values consisting of the residual torque and the corresponding rotation angle of said lever body, and in that said first interface means (12, 13) comprise signalling means to a user of the detection of the pair of values consisting of the residual torque and the corresponding rotation angle of said lever body which can be actuated by said processing unit wherein the detection of the pair of values corresponding to the moment when said threaded fastening element begins to move comprises:
   processing the pairs of values consisting of torque and corresponding rotation angle of the lever body ($T_i$, $A_i$) acquired by the respective sensor means for obtaining pairs of values consisting of the average values of torque and corresponding rotation angle of the lever body ($T_m$, $A_m$),
   processing the pairs consisting of the average values ($T_m$, $A_m$) of torque and corresponding rotation angle of the lever body so obtained in order to determine the angular coefficient ($\alpha_t$) of the curve given by said average values of torque ($T_m$) in function of the corresponding average values of the rotation angle ($A_m$) of the lever body,
   processing the values of angular coefficient ($\alpha_t$) so obtained for obtaining an average value of angular coefficient ($\alpha_m$).

2. The system (1) according to claim 1, characterized in that said processing unit (9) works in real time with said wrench.

3. The system (1) according to claim 1, characterized in that said processing unit (9) is integrated in said lever body (2) or in a separate body (20) from said lever body and connectable with it, wherein said separate body comprises second interface means (10, 11).

4. The system (1) according to claim 1, characterized in that said signalling means are of the visual and/or acoustic and/or vibration type.

5. The system (1) according to claim 1, characterised in that the detection of the pair of values corresponding to the moment when said threaded tightening element begins to move also comprises:

discriminating among the average values of angular coefficient ($\alpha_m$) so obtained a sequence of N strictly decreasing values;

verifying whether the percentage variation between the average values of angular coefficient ($\alpha_m$) corresponding to the extremes of said sequence of N values exceeds a predefinable threshold ($\delta\%$) and, in the positive case, identifying an angular coefficient intermediate between said extremes and attributing to the pair of values corresponding to the moment when said threaded tightening element begins to move, the values of average torque ($T_m$) and the corresponding average rotation angle ($A_m$) of the lever body corresponding to said intermediate angular coefficient, and in the negative case, repeating the verification for a subsequent sequence of N values strictly decreasing.

6. The system according to claim 5, characterized in that said verifying if the percentage variation between the average values of angular coefficient ($\alpha_m$) corresponding to the extremes of said sequence of N strictly decreasing values exceeds a predefinable threshold ($\delta\%$), consists in applying the following formula $$(\alpha_{m-N+1} - \alpha_m) > (\alpha_{m-N+1} * \delta) \backslash 100$$

where $\alpha_{m-N+1} > \alpha_{m-N+2} > \ldots > \alpha_{m-2} > \alpha_{m-1} > \alpha_m$.

7. System (1) according to claim 5, characterised in that the discrimination, among the pairs of values subsequent to and comprising the pair of value of the start of the movement identified and comprised in a predefinable variability range of said rotation angle of said lever body, the pair of values consisting of the residual torque and the corresponding rotation angle of said lever body comprises:

attributing to the pair of values consisting of the residual torque and the corresponding rotation angle of said lever body the values of torque and of the corresponding rotation angle of said lever body corresponding to the pair identified as that corresponding to the moment when said threaded tightening element begins to move;

verifying if, in a number P of average values of angular coefficient ($\alpha_m$) subsequent to said sequence of N values or subsequent to said pair $P_D=(Tm, Am)_D$, the average values of said angular coefficient ($\alpha_m$) are all positive and, in the positive case, confirming the identified pair as that corresponding to the moment when said threaded tightening element begins to move as said pair of values consisting of the residual torque and the corresponding rotation angle of said lever body and, in the negative case, detecting, starting from the negative average value of the angular coefficient ($\alpha_m$), a sequence of Q values wherein said average values of the angular coefficient return to be positive and strictly increasing and attributing to the pair of values consisting of the residual torque and the corresponding rotation angle of said lever body the values of the torque and of the corresponding rotation angle of said lever body corresponding to the first of said Q values.

8. The system (1) according to claim 1, characterized in that the identification of the pair of values corresponding to the moment when said threaded tightening element begins to move also comprises:

considering pairs of values $P_i=(Tm, Am)_i$ consisting of the average values of torque and corresponding rotation angle of the lever body (Tm, Am) by successive increments $\Delta A$ of the rotation angle of the lever body;

for each pair $P_i=(Tm, Am)_i$ determining the distance Di of the point identified by it from the straight line that joins the first of said pairs $P_1=(Tm, Am)_1$ with the last of said pairs $P_u=(Tm, Am)_u$ according to the following formula:

$$Di = (A_{mu} - A_{m1}) \times (T_{m1} - T_{mi}) - (A_{m1} - A_{mi}) \times (T_{mu} - T_{m1})$$

selecting among the pairs $P_i=(Tm, Am)_i$ the one $P_{max}$ the value of said distance Di of which is the greatest ($D_{max}$);

discriminating in a "window" of H pairs $P_i=(Tm, Am)_i$ subsequent to and comprising $P_{max}$, from $P_{max}$ (Tm, Am)$_{max}$ to $P_{max+H}=(Tm, Am)_{max+H}$, the pair $P_D=(Tm, Am)_D$ the gradient of which is the lowest according to the following formula:

$$\min(T_{m(k+1)} - T_{m(k)}) \text{ with } \max < k < \max + (H-1)$$

for each pair $P_i=(Tm, Am)_i$ acquired repeating the previous steps and checking whether for the subsequent X pairs $P_i=(Tm, Am)_i$ acquired the current value of $P_D$ coincides with that determined for the previous pair $P_i=(Tm, Am)_i$ and, in the positive case, attributing to the pair of values corresponding to the moment when said threaded tightening element begins to move, the values of average torque ($T_m$) and the corresponding average rotation angle ($A_m$) of such a pair $P_D=(Tm, Am)_D$.

9. The system (1) according to claim 1, characterized in that said processing of the pairs of values consisting of torque and corresponding rotation angle of the lever body ($T_i, A_i$) acquired by the respective sensor means in order to obtain pairs of values consisting of the average values of torque and corresponding rotation angle of the lever body ($T_m, A_m$) comprises applying to said pairs of acquired values ($T_i, A_i$) a moving "window" average having width equal to I samples in order to obtain pairs of values consisting of the average values of torque and corresponding rotation angle of the lever body ($T_m, A_m$), where $$T_m = \frac{\sum_{i=1}^{I} T_i}{I} \text{ and } A_m = \frac{\sum_{i=1}^{I} A_i}{I}.$$

10. The system according to claim 1, characterized in that said processing of the pairs consisting of the average values ($T_m, A_m$) of torque and corresponding rotation angle of the lever body in order to determine the angular coefficient ($\alpha_t$) of the curve given by said average values of torque ($T_m$) in function of the corresponding average values of rotation angle ($A_m$) of the lever body comprises applying to said pairs of average values ($T_m, A_m$) a linear regression according to following formula $$\alpha_t = \left( \left( \sum_{m=1}^{M} T_m \times A_m \right) - \frac{\sum_{m=1}^{M} T_m \times \sum_{m=1}^{M} A_m}{M} \right) / \left( \left( \sum_{m=1}^{M} A_m^2 \right) - \frac{\sum_{m=1}^{M} A_m \times \sum_{m=1}^{M} A_m}{M} \right)$$

11. The system according to claim 1, characterized in that said processing of the values of angular coefficient ($\alpha_t$) so obtained in order to obtain an average value of angular coefficient ($\alpha_m$), comprises applying to said values of angular coefficient ($\alpha_t$) a moving "window" average equal to T samples in order to obtain an average value of angular coefficient ($\alpha_m$) wherein $$\alpha_m = \frac{\sum_{t=1}^{T} \alpha_t}{T}$$

12. A method for the quality control of screwed-in joints, comprising the phases consisting in:
   a) providing a system comprising:
      an electronic dynamometric wrench comprising a lever body (2) provided, at one end, with a handle (3) and, at the opposite end, with a coupling head (4) with the threaded tightening element of the joint to be controlled, sensor means (6) of the torque applied to said threaded tightening element which are associated with said lever body (2) and which are suitable for supplying an output signal corresponding to the torque applied to the threaded tightening element from said lever body and sensor means (7) of the rotation angle of said lever body (2) which are associated with said lever body and which are suitable for supplying an output signal corresponding to the rotation angle of said lever body when applying said torque,
      first interface means (12, 13) with an user which are associated with said lever body and which comprise signalling means,
      a processing unit (9) in communication with said sensor means (6) of the torque and said sensor means (7) of the rotation angle of said lever body (2), from which it receives in input the respective output signals, and with said first interface means with a user,
   b) applying, by means of said dynamometric wrench, a torque to the threaded tightening element of a joint to be controlled in the rotation direction corresponding to the tightening of the same and acquiring, through said sensor means (6, 7), the values of applied torque ($T_i$) and of the corresponding rotation angle ($A_i$) of said lever body,
   c) identifying, among the pairs of values consisting of torque and corresponding rotation angle of the lever body acquired from said respective sensor means, the pair of values corresponding to the moment when said threaded tightening element begins to move,
   d) discriminating, among the pairs of values subsequent to and comprising the pair of values of the start of the movement so identified and comprised in a predefinable variability range of said rotation angle of said lever body, the pair of values consisting of the residual torque and the corresponding rotation angle of said lever body, and
   e) signalling to a user the detection of the pair of values consisting of the residual torque and the corresponding rotation angle of said lever body through said first signalling means, wherein said phase c) of identifying of the pair of values corresponding to the moment when said threaded tightening element begins to move comprises the steps consisting in:
      processing the pairs of values consisting of torque and corresponding rotation angle of the lever body ($T_i$, $A_i$) acquired by the respective sensor means in order to obtain pairs of values consisting of average values of torque and corresponding rotation angle of the lever body ($T_m$, $A_m$),
      processing the pairs consisting of the average values ($T_m$, $A_m$) torque and corresponding rotation angle of the lever body so obtained in order to determine the angular coefficient ($\alpha_t$) of the curve given by said average values of torque ($T_m$) in function of the corresponding average values of rotation angle ($A_m$) of the lever body,
      processing the values of angular coefficient ($\alpha_t$) so obtained in order to obtain an average value of the angular coefficient ($\alpha_m$).

13. The method according to claim 12, wherein said processing unit (9) is integrated in said lever body (2) or in a separate body (20) from said lever body and connectable with it, said separate body comprising second interface means, and wherein said phases c), d) and e) occur in real time with said phase b).

14. The method according to claim 12, wherein said step c) of identifying the pair of values corresponding to the moment when said threaded tightening element begins to move also comprises the steps consisting in:
   considering pairs of values $P_i=(Tm, Am)_i$ consisting of the average values of torque and corresponding rotation angle of the lever body (Tm, Am) by successive increments $\Delta A$ of the rotation angle of the lever body;
   for each pair $P_i=(Tm, Am)_i$ determining the distance Di of the point identified by it from the straight line that joins the first of said pairs $P_1=(Tm, Am)_1$ with the last of said pairs $P_u=(Tm, Am)_u$ according to the following formula:

$$Di = (A_{mu} - A_{m1}) \times (T_{m1} - T_{mi}) - (A_{m1} - A_{mi}) \times (T_{mu} - T_{m1})$$

selecting among the pairs $P_i=(Tm, Am)_i$ the one $P_{max}$ the value of said distance Di of which is the greatest ($D_{max}$);
   discriminating in a "window" of H pairs $P_i=(Tm, Am)_i$ subsequent to and comprising $P_{max}$, from $P_{max}(Tm, Am)$ to $P_{max+H}=(Tm, Am)_{max+H}$, the pair $P_D=(Tm, Am)_D$ the gradient of which is the lowest according to the following formula:

$$\min(T_{m(k+1)} - T_{m(k)}) \text{ with } max < k < max+(H-1)$$

for each pair $P_i=(Tm, Am)_i$ acquired repeating the previous steps and checking whether for the subsequent acquired X pairs $P_i=(Tm, Am)_i$ the current value of $P_D$ coincides with that determined for the previous pair $P_i=(Tm, Am)_i$ and, in the positive case, attributing to the pair of values corresponding to the moment when said threaded tightening element begins to move, the values of average torque ($T_m$) and the corresponding average rotation angle ($A_m$) of such a pair $P_D=(Tm, Am)_D$.

15. The method according to claim 12, wherein said step consisting in processing the pairs of values consisting of torque and corresponding rotation angle of the lever body ($T_i$, $A_i$) acquired by the respective sensor means in order to obtain pairs of values consisting of the average values of torque and corresponding rotation angle of the lever body ($T_m$, $A_m$), comprises applying to said acquired pairs of values ($T_i$, $A_i$) a moving "window" average having width equal to I samples in order to obtain pairs of values consisting of average values of torque and corresponding rotation angle of the lever body ($T_m$, $A_m$), where $$T_m = \frac{\sum_{i=1}^{I} T_i}{I} \text{ and } A_m = \frac{\sum_{i=1}^{I} A_i}{I}.$$

16. The method according to claim 12, wherein said step consisting in processing the pairs consisting of the average values ($T_m$, $A_m$) of torque and corresponding rotation angle of the lever body in order to determine the angular coefficient ($\alpha_t$) of the curve given by said average values of torque ($T_m$)

in function of the corresponding average values of rotation angle ($A_m$) of the lever body, comprises applying to said pairs of average values ($T_m$, $A_m$) a linear regression according to the following formula $$\alpha_t = \left(\left(\sum_{m=1}^{M} T_m \times A_m\right) - \frac{\sum_{m=1}^{M} T_m \times \sum_{m=1}^{M} A_m}{M}\right) \Big/ \left(\left(\sum_{m=1}^{M} A_m^2\right) - \frac{\sum_{m=1}^{M} A_m \times \sum_{m=1}^{M} A_m}{M}\right).$$

17. The method according to claim 12, wherein said step consisting in processing the values of angular coefficient ($\alpha_t$) so obtained in order to obtain an average value of angular coefficient ($\alpha_m$) comprises applying to said values of angular coefficient ($\alpha_t$) a moving "window" average equal to T samples in order to obtain an average value of angular coefficient ($\alpha_m$) wherein $$\alpha_m = \frac{\sum_{t=1}^{T} \alpha_t}{T}.$$

18. The method according to claim 12, wherein said step c) of identifying the pair of values corresponding to the moment when said threaded tightening element begins to move also comprises the steps consisting in:
discriminating among the average values of angular coefficient ($\alpha_m$) so obtained a sequence of N strictly decreasing values;
verifying whether the percentage variation between the average values of angular coefficient ($\alpha_m$) corresponding to the extremes of said sequence of N values exceeds a predefinable threshold ($\delta\%$) and, in the positive case, identifying an angular coefficient intermediate between said extremes and attributing to the pair of values corresponding to the moment when said threaded tightening element begins to move, the values of average torque ($T_m$) and the corresponding average rotation angle ($A_m$) of the lever body corresponding to said intermediate angular coefficient, in the negative case, repeating the verification for a subsequent sequence of N strictly decreasing values.

19. The method according to claim 18, wherein said step consisting in verifying whether the percentage variation between the average values of angular coefficient ($\alpha_m$) corresponding to the extremes of said sequence of N strictly decreasing values exceeds a predefinable threshold ($\delta\%$), consists in applying the following formula:

$$(\alpha_{m-N+1} - \alpha_m) > (\alpha_{m-N+1} * \delta) \backslash 100$$

where $\alpha_{m-N+1} > \alpha_{m-N+2} > \ldots > \alpha_{m-2} > \alpha_{m-1} > \alpha_m$.

20. The method according to claim 12, wherein said step of discriminating d), among the pairs of values subsequent to and comprising the identified pair of values of the start of the movement and included in a predefinable variability range of said rotation angle of said lever body, the pair of values consisting of the residual torque and the corresponding rotation angle of said lever body comprises the steps consisting in:
attributing to the pair of values consisting of the residual torque and the corresponding rotation angle of said lever body the values of torque and of the corresponding rotation angle of said lever body corresponding to the pair identified as the one corresponding to the moment when said threaded tightening element begins to move;
verifying whether, in a number P of average values of angular coefficient ($\alpha_m$) subsequent to said sequence of N values or subsequent to said pair $P_D = (Tm, Am)_D$, the average values of said angular coefficient ($\alpha_m$) are all positive and, in the positive case, confirming the identified pair as the one corresponding to the moment when said threaded tightening element begins to move as said pair of values consisting of the residual torque and the corresponding rotation angle of said lever body and, in the negative case, detecting, starting from the negative average value of the angular coefficient ($\alpha_m$), a sequence of Q values wherein said average values of the angular coefficient return to be positive and strictly increasing and attributing to the pair of values consisting of the residual torque and the corresponding rotation angle of said lever body the values of the torque and of the corresponding rotation angle of said lever body corresponding to the first of said Q values.

* * * * *